United States Patent [19]

Arcuri et al.

[11] 4,413,058
[45] Nov. 1, 1983

[54] **CONTINUOUS PRODUCTION OF ETHANOL BY USE OF FLOCCULENT *ZYMOMONAS MOBILIS***

[75] Inventors: Edward J. Arcuri, Del Mar, Calif.; Terrence L. Donaldson, Lenoir City, Tenn.

[73] Assignee: The United States of America as represented by the U.S. Department of Energy, Washington, D.C.

[21] Appl. No.: 343,610

[22] Filed: Jan. 28, 1982

[51] Int. Cl.³ ............................................... C12P 7/06
[52] U.S. Cl. .................................... 435/161; 435/284; 435/296; 435/313; 435/813
[58] Field of Search ........ 435/161, 162, 163, 254–255, 435/101, 296, 313, 813, 284

[56] References Cited

U.S. PATENT DOCUMENTS 3,406,114  10/1968  Goren ............................. 435/101 X
4,350,765   9/1982  Chibata et al. ..................... 435/161

OTHER PUBLICATIONS

Rogers et al., "*High Productivity Ethanol Fermentations with Zymomonas Mobilis*", Process Biochemistry Aug.-/Sep. 1980, pp. 7–8 and 10.
Skotnicki et al., "Comparison of Ethanol Production by Different Zymomonas Strains", Chemical Abstracts, No. 95:5105j, (1981).

*Primary Examiner*—R. B. Penland
*Attorney, Agent, or Firm*—Edwin D. Grant; Stephen D. Hamel; Richard G. Besha

[57] ABSTRACT

Ethanol is produced by means of a floc-forming strain of *Zymomonas mobilis* bacteria. Gas is vented along the length of a column containing the flocculent bacteria to preclude disruption of liquid flow.

4 Claims, 4 Drawing Figures

4,413,058

CONTINUOUS PRODUCTION OF ETHANOL BY USE OF FLOCCULENT ZYMOMONAS MOBILIS

BACKGROUND OF THE INVENTION

The invention disclosed herein resulted from a contract with the United States Department of Energy and relates to the production of ethanol by a continuous-flow fermentation process and apparatus for conducting this process.

In one previously used process for producing ethanol, a sugar-containing solution is continuously added to a stirred vessel (or reactor) in which yeast or other micoorganisms that convert sugar to ethanol circulate freely. The effluent continuously withdrawn from such stirred reactors contains both the ethanol product and some of the microorganisms, and to make the process economically feasible the microorganisms must be separated from the effluent and recycled to the reactor. The initial capital outlay and operating costs for the equipment required for this separation are not the only disadvantages in the use of stirred reactors, for the concentration of ethanol in such apparatus can rise to a level which inhibits the activity of the alcohol-producing microorganisms used therein. Stirred reactors have been operated under reduced pressure to minimize this inhibition problem by vaporization of the ethanol, but the equipment required for this purpose is complex and also represents a major expense in terms of capital outlay and operating costs.

To avoid the above-described problems, various means have been proposed for immobilizing alcohol-producing microorganisms in a reactor through which a sugar-containing solution is continuously passed. Microorganisms have previously been immobilized by (1) providing reactor packings to which microorganisms have a natural ability to attach, (2) chemically bonding microorganisms to reactor packings, and (3) interspersing microorganisms in porous reactor packings. However, as is well known to microbiologists, different microorganisms vary considerably with respect to their ability to attach to reactor packings, and some materials which have been used as bonding agents or supports for immobilizing microorganisms require extensive preparation before use.

SUMMARY OF THE INVENTION

It is an object of this invention to provide an improved means and process for producing ethanol by fermentation.

Another object of the invention is to produce ethanol in a continuous-flow process by means of a biological catalyst that can be retained in a continuous-flow reactor vessel without being bonded to or held within a support material.

An additional object of the invention is to provide a fermentation reactor vessel wherein disturbance of the desirable plug flow of sugar solution is minimized.

These objects are attained by the preferred apparatus and process of the invention which utilize a newly-discovered flocculent strain of Zymomonas mobilis (hereinafter referred to as Z. mobilis for brevity) for converting sugar to ethanol in a continuous flow-type reactor vessel. The flow rate of a sugar-containing solution through a column containing the floc-forming strain of Z. mobilis is adjusted so that a sufficient conversion of sugar to ethanol is achieved in the column and the flocculent Z. mobilis is not washed away in effluent from the column. Carbon dioxide gas generated by the fermentation process is vented from a plurality of points spaced along an inclined column in which the process is conducted, thus minimizing disturbance of the plug flow of liquid by this gas.

Figure 1:
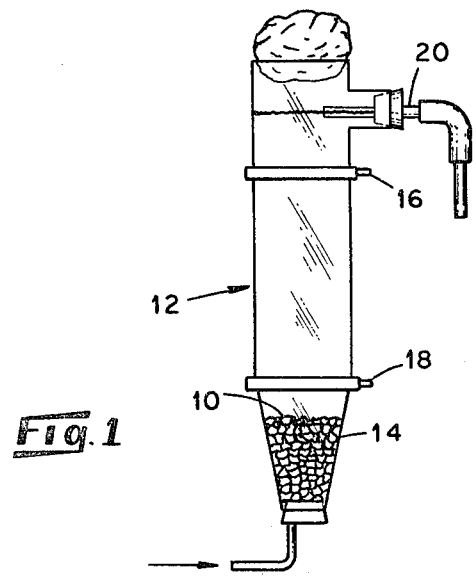
FIG. 1 is a diagrammatic representation of the apparatus used in testing the efficiency of an ethanol-producing process in accordance with the applicants' invention.

DETAILED DESCRIPTION OF PREFERRED APPARATUS AND PROCESS EMBODIMENTS OF THE INVENTION

The effectiveness of strains of Zymomonas mobilis for converting sugar to ethanol has been previously reported by P. J. Rogers et al in an article entitled "High Productivity Ethanol Fermentations with Zymomonas Mobilis", published in the August/September 1980 issue of Process Biochemistry. Researchers at the Oak Ridge National Laboratories in Oak Ridge, Tenn., including the inventors named in this application, have been engaged in developmental programs directed toward determining effective means for immobilizing biological catalysts on or in packings for continuous-flow apparatus for producing ethanol by fermentation. In connection with these investigations, a strain of Z. mobilis identified as ATCC No. 10988 was obtained from the American Type Culture Collection, 12301 Parklawn Drive, Rockville, Md., during the month of July, 1980. Subsequently various materials were tested by the applicants to determine their efficacy in immobilizing cultures of the above-identifed strain of Z. mobilis. Furthermore, during approximately 14 fermentation tests conducted with cultures of the ATCC No. 10988 Z. mobilis, applicants observed no tendency of the microorganism to flocculate. However, after this period of experimentation with ATCC No. 10988 cultures under various fermentation conditions, the applicants observed during one test (which will be described in detail hereinafter) that macroscopic floc particles of one Z. mobilis culture were spontaneously formed in a continuously flowing aqueous stream containing sugar and other nutrients. This particular Z. mobilis strain has been isolated and maintained by means of conventional techniques which are well known by microbiologists, and a sample of the strain is deposited in the Agricultural Research Culture Collection, International Depository Authority (NRRL), 1815 N. University Street, Peoria, Ill., and registered therein as Zymomonas mobilis "f", International Depository Authority accession number NRRL B-12526. As will be shown in the following test examples, the fermentation of sugar by use of the form of Z. mobilis which has been found by applicants to flocculate in a continuous-flow reactor vessel provides the important advantage of eliminating any need for a separate means for immobilizing the biological catalyst on a packing.

EXAMPLE I

*Zymomonas mobilis* ATCC 10988 was maintained on a liquid medium comprising 5.0 grams of glucose and 0.5 gram of yeast extract per 100 ml of water. Yeast extract is a well known nutrient for bacteria cultures and it is available from the Difco Company and other sources. For ethanol production studies in the reactor illustrated in FIG. 1, the same concentration of yeast extract was used; however, the concentration of glucose in this case was either 5.0 or 10.0 grams per 100 ml of water. A flask containing 100 ml of the growth medium (5 grams of glucose per 100 ml of water for one test, and 10 grams of glucose per 100 ml of water for a second test) was innoculated with 1.0 ml of the above-described culture of *Z. mobilis* ATCC 10988. These cultures were incubated at 30° C. for 48 h in a gyratory shaker and then used as starting cultures in the experimental reactor.

A flocculent bioreactor was constructed by adding approximately 10.0 ml of polystyrene beads 10 (1.0 mm diameter) to the bioreactor 12 depicted in FIG. 1. The total reactor height was 58.42 cm. The bottom glass section 14 of the column had a length of 22.86 cm and an internal diameter varying from 2.54 cm at the top to an internal diameter of 1.27 cm at the base. The remainder of the column had an internal diameter of 2.54 cm. Sampling ports 16,18 were located where shown in the drawing. The column was connected to a glass tube 20 and sterilized by autoclaving at 121° C. and 15 psi for 25 min.

Ten milliliters of a portion of the above-described *Z. mobilis* ATCC 10988 culture which had been incubated at 30° C. for 48 hours and 10.0 ml of the above-described growth medium containing 5 grams glucose per 100 ml water were added to the described reactor. The bioreactor was kept at room temperature (approximately 24° C.). At 1 day intervals, on three successive days, the medium contained in the bioreactor was drained down to the top of the bed (i.e., the styrene beads just remained submerged). A volume of 10.0 ml of the above-described growth medium was then added to the column. After 24 hours, a continuous flow (1.8 to 10.0 ml/min) of the above-described aqueous solution containing either 5.0 grams or 10.0 grams of glucose and 0.5 gram of yeast extract per 100 ml $H_2O$ was metered through the column using a peristaltic pump. At daily intervals, samples were withdrawn, clarified by centrifugation at $1000 \times g$ for 10 min at 4° C., and the supernatants analyzed for ethanol and glucose.

During the startup phase (i.e., during the period of daily batch-feeding of *Z. mobilis* ATCC 10988 culture) of the reactor, samples of the polystyrene beads were aseptically removed and observed by phase contrast microscopy. No evidence of significant attachment to the beads was observed. However, a marked tendency toward bacterial floc formation was observed. Once continuous operation of the bioreactor was initiated, floc formation became more pronounced. The size of the individual floc particles reaches macroscopic dimensions (approximately 1.0 mm in diameter), and the density of the particles was such that a volumetric flow rate of 10.0 ml/min tended only to expand the bed and did not wash the floc out of the bioreactor. As was observed in the startup phase of operation, there was no apparent attachment to the styrene beads.

Figure 2:
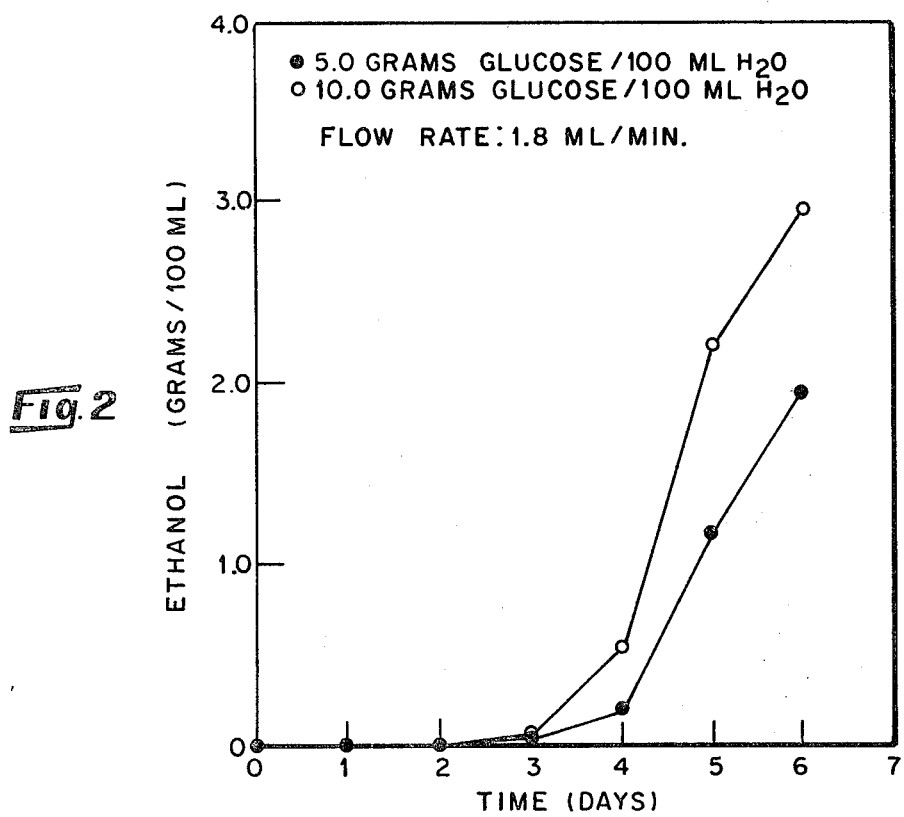
FIG. 2 is a graph illustrating the rate of ethanol production achieved in test conducted with the apparatus of FIG. 1.

The above pattern of floc formation and lack of attachment to the styrene beads was noted when either the solution containing 5.0 grams of glucose per 100 ml of water or the solution containing 10.0 grams of glucose per 100 ml of water was employed. The concentrations of ethanol produced at the two glucose concentrations are shown in FIG. 2. In both cases, the volumetric flow rate of the medium through the bioreactor was 1.8 ml/min. In this graph, day 0 represents the time at which continuous operation of the bioreactor was initiated. From the figure, it can be seen that no ethanol was detected during the first two days of operation. However, by day 3 a small but significant amount of ethanol was found and the concentration of ethanol in the effluent stream increased dramatically thereafter. The residual glucose profiles (data not given) during the courses of the experiments were as expected (i.e., no glucose removal was detected during the first two days of operation, but the residual glucose levels fell off rapidly during the remainder of the experiment). The rapid increase in ethanol concentrations observed after day 3 was accompanied by a dramatic increase in the amount of flocculent biomass observed in the bioreactor. The productivities (in grams ethanol produced/liters of reactor volume·hour) calculated from the ethanol levels observed on day 6 are given in the following table.

| REACTOR PRODUCTIVITIES OF THE FLOCCULENT BIOREACTOR ILLUSTRATED IN FIG. 1 | | | |
|---|---|---|---|
| Grams glucose per 100 ml $H_2O$ | Flow Rate (ml/min) | % Ethanol (Effluent) | Productivity (g/l · hr) |
| 5 | 1.8 | 1.97 | 70.8 |
| 5 | 10.0 | 0.66 | 132.0 |
| 10 | 1.8 | 2.96 | 79.9 |
| 10 | 10.0 | 0.80 | 120.0 |

The productivities obtained at a flow rate of 1.8 ml/min were 70.8 and 79.9, respectively, for the 5.0 grams glucose per 100 ml $H_2O$ and the 10.0 grams glucose per 100 ml $H_2O$ feeds. The values for reactor volume used in these productivity calculations were those defined by the geometric boundary of the expanded bed (0.03 and 0.04 l for the 5.0 gram and 10.0 gram glucose concentration cases, respectively). It was shown that no measurable change in ethanol concentration occurred between the top of the expanded bed and the reactor vessel liquid outlet port.

Reactor operation at a flow rate of 1.8 ml/min was not continued past day 6 due to problems arising from continued microbial growth. That is, as rapid accumulation of dense flocculent biomass occurred, a flow rate of 1.8 ml/min was unable to maintain the bed in an "expanded" state. Medium channeling and gas ($CO_2$) bubble accumulation occurred with intermittent turbulent disruption of the bed by the disengagement of large gas bubbles. This problem was alleviated by increasing the volumetric flow rate to 10.0 ml/min. The 5.6-fold increase in flow rate only resulted in a 3.0-fold and 3.7-fold decrease in the concentration of ethanol in the effluent stream when the column was fed 5.0 and 10.0% glucose, respectively. As shown in the above table, the increase in flow rate thus led to an increase in reactor productivity to 132.0 g/l·hr and 120.0 g/l·hr for the reactors being fed the described 5.0 grams and 10.0 grams glucose per 100 ml $H_2O$, respectively.

EXAMPLE II

Figure 3:
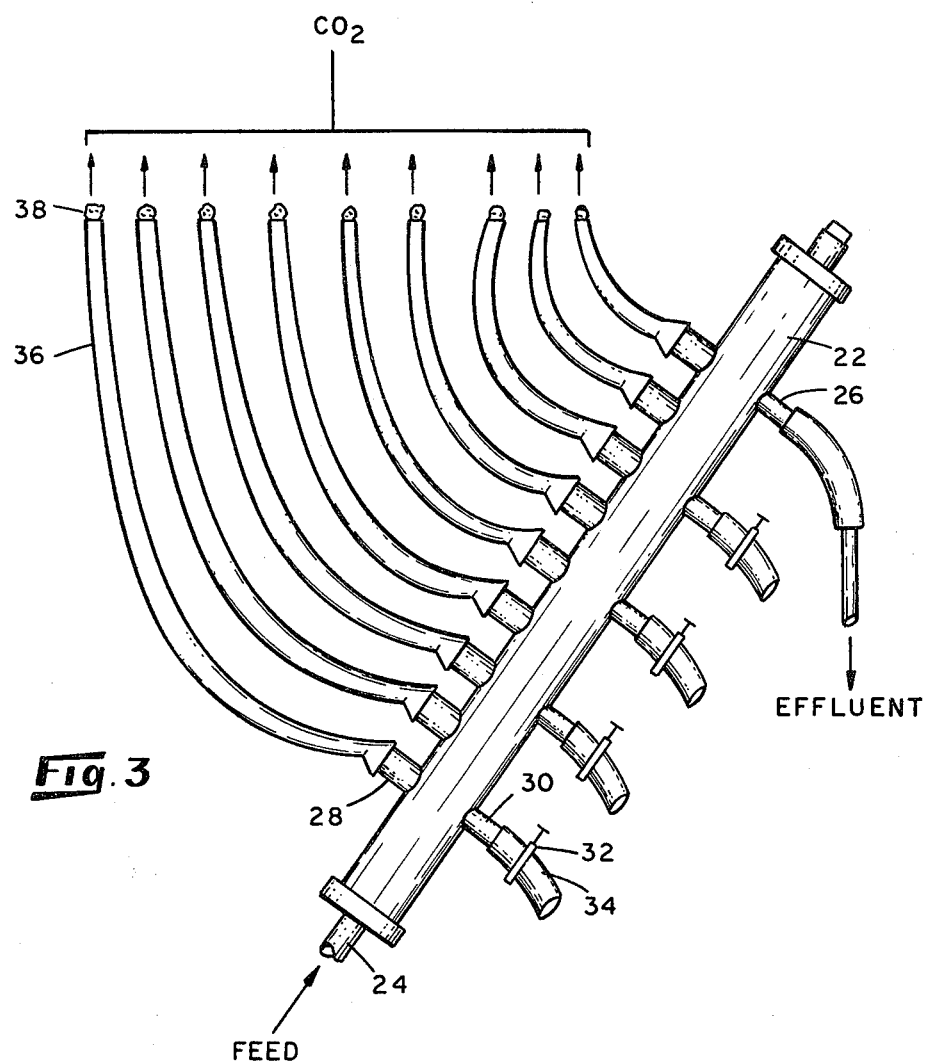
FIG. 3 is a diagrammatic representation of a preferred apparatus for producing ethanol in accordance with the applicants' invention.

FIG. 3 illustrates a preferred apparatus for use in producing ethanol with the floc-forming *Z. mobilis* "f"

Figure 4:
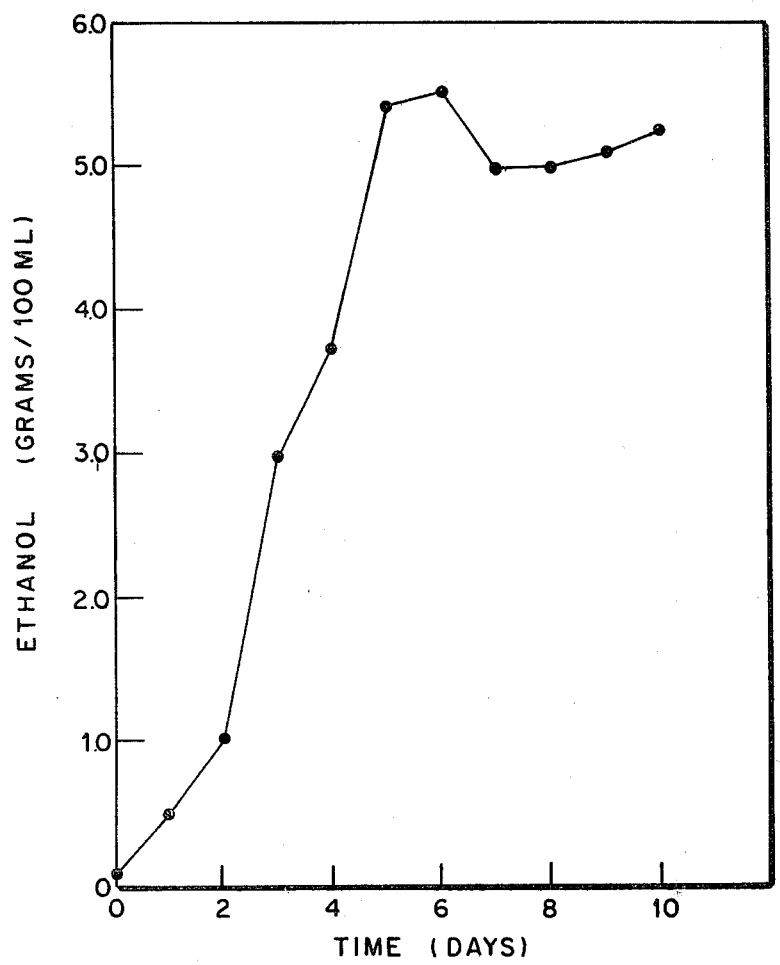
FIG. 4 is a graph illustrating the rate of ethanol production in tests conducted with the apparatus of FIG. 3.

NRRL B-12526 discovered by applicants. The apparatus comprises a tubular column 22 which in the drawing is inclined at an angle of approximately 45° relative to a horizontal plane. However, tests have shown that the gas-venting advantage attained by use of column 22 (which will be further described hereinafter) is not limited to a placement of the column at 45° relative to a horizontal plane. In fact, it has been found that the column can be used effectively in near-horizontal and near-vertical positions as well as in positions therebetween. Feed is introduced into column 22 through a conduit 24 at its lower end and effluent is discharged from the column through a conduit 26 at its upper end. Fixedly attached to the column and spaced apart along one side thereof are a number of conduits 28, these conduits communicating with the interior of the column through apertures in the wall of the column. Sampling conduits 30 are likewise attached to the column and spaced apart along the side thereof opposite the vent conduits. Flow through sampling conduits 30 is controlled by spring clamps 32 mounted on resilient tubes 34 attached to the conduits. Extension tubes 36 connected to vent conduits 28 project upward to a level even with or above the upper end of column 22. In claims appended hereto, conduits 28 and the extension tubes 36 associated therewith are referred to as gas-venting conduits. A filter 38 (e.g., a wad of cotton) is positioned in the upper end of each extension tube 36 to maintain the sterility of column 22. The above-described column was initially filled with approximately 50 ml of a sterile solution containing 10 grams of glucose and 0.5 gram of yeast extract per 100 ml of water. A culture of the floc-forming strain of Z. mobilis "f" NRRL B-12526 discovered by the applicants in the experiment described in Example I was prepared by allowing a portion of the strain to grow for 24 hours in 100 ml of the same 10 grams glucose-0.5 gm yeast extract per 100 ml H₂O solution, the solution being maintained at 30° C. during the growth period. The reactor illustrated in FIG. 3 was then innoculated with 20 ml of the aforesaid 24 hour incubation culture. After 24 hours, a significant microbial film was found loosely attached to the wall of the reactor. Then a solution containing 10 grams of glucose and 0.5 gram of yeast extract per 100 ml H₂O was pumped through the reactor at a flow rate of 2.0 ml/min by means of a peristaltic pump. After 4 hours, a sample of the effluent from the reactor was taken and the ethanol concentration therein was determined. The ethanol concentration in the effluent was subsequently determined at daily intervals. The trend in ethanol production over the ten-day period is shown in FIG. 4. During the course of the run, the glucose concentration was increased to 17 grams per 100 ml of water. It can be seen that the ethanol concentration increased rapidly during the first five days of reactor operation and subsequently leveled off at an average value of 5.2%. This corresponds to a volumetric productivity of 125 grams of ethanol per reactor volume (in liters) per hour.

During the first 24 hours of reactor operation, the film of Z. mobilis "f" NRRL B-12526 which was found loosely attached to the walls of the reactor fell away in large, loose clumps and settled to the bottom of the reactor. Within the first 2-3 days of operation, the clumps began to break up and form smaller and more tightly packed floc particles. The reason for the film breakup is not clear, but probably is the result of the combined effects of continued cell growth and the associated liberation of large amounts of $CO_2$. Upon continued reactor operation, the total amount of flocculent biomass increased rapidly and reached a maximum volume of approximately 50 ml on day 5. This amount of biomass filled the reactor to just above the second gas vent and did not appear to increase past 50 ml for the duration of the experimental run.

The combination of the floc-forming strain of Z. mobilis "f" NRRL B-12526 bacteria with the gas venting reactor 22 illustrated in FIG. 3 provides a less cumbersome and more efficient process for continuous ethanol production than prior art processes. The use of the gas venting bioreactor 22 with the floc-forming Z. mobilis prevents the disruption of the plug flow nature of the reactor system by conducting the $CO_2$ generated during ethanol fermentation away from the reaction zone near the point of origin of the gas instead of allowing it to traverse the length of the column. Maintenance of the plug flow nature restricts the region of high ethanol concentration to a small zone near the exit of the reactor. The lower ethanol concentrations throughout the inlet and mid regions of the reactor are less inhibitory to the Z. mobilis "f" NRRL B-12526; hence ethanol is produced at higher rates which leads to an overall more efficient reactor system.

The applicants are not aware of any prior publication or other disclosure concerning a strain of Z. mobilis bacteria which flocculates in a continuously flowing stream containing sugar, and the Z. mobilis strain ATCC No. 10988 obtained from the American Type Culture Collection did not flocculate during the initial experiments made by the applications with the same type of sugar-containing feeds and reactor flow conditions disclosed herein. However, it is well known that mutations occur in bacteria either naturally or as a result of some environmental influence exerted thereon.

What is claimed is:

1. A method for producing ethanol, comprising:
    placing flocculent Zymomonas mobilis "f" NRRL B-12526 in a reactor column; and
    passing a stream containing water, sugar, and yeast extract through said reactor column at a flow rate which permits conversion of sugar in said stream to ethanol in said column and retention of said flocculent Zymomonas mobilis "f" NRRL B-12526 in said reactor column.

2. The method of claim 1 wherein the sugar in said stream is glucose.

3. The method of claim 1 wherein said stream contains about 5 to about 17 grams of glucose and about 0.5 gram of yeast extract per 100 milliliters of water.

4. A means for producing ethanol, comprising:
    a tubular vessel through which is passed a stream containing water, sugar, and yeast extract, the longitudinal axis of said vessel being disposed at an angle of about 45° relative to a horizontal plane;
    a plurality of gas venting conduits attached to and spaced apart along said vessel and communicating with the interior thereof, free ends of said gas venting conduits terminating at a level substantially even with or above the upper end of said vessel; and
    a flocculent mass of Zymomonas mobilis "f" NRRL B-12526 disposed in said vessel for converting said sugar to ethanol.

* * * * *